United States Patent

Yoo

[11] Patent Number: 5,948,506
[45] Date of Patent: Sep. 7, 1999

[54] MOXIBUSTING IMPLEMENT

[76] Inventor: Tae Woo Yoo, 807, 1-Dong, Hanyang, Apt. 32-5, Banpo-dong, Seocho-ku, Seoul, Rep. of Korea

[21] Appl. No.: 09/131,060

[22] Filed: Aug. 6, 1998

[30] Foreign Application Priority Data

Jun. 15, 1998 [KR] Rep. of Korea ............ 98-10171

[51] Int. Cl.$^6$ .................................................. B32B 3/24
[52] U.S. Cl. ................. 428/139; 428/137; 428/138; 428/224; 428/913; 604/24; 604/291; 604/304
[58] Field of Search ............................ 428/137, 138, 428/139, 224, 913; 604/291, 304, 24

[56] References Cited

U.S. PATENT DOCUMENTS 5,549,960   8/1996   Woo .......................................... 428/139

Primary Examiner—Christopher Raimund
Attorney, Agent, or Firm—Richard M. Goldberg

[57] ABSTRACT

A moxibusting implement includes a loess support having a receiving hole and a recess for inserting a filter paper. When a moxa is burned and the heat generated reaches the loess support(10), far-infrared radiation is produced from the loess support to enhance the effect of the moxa cautery treatment.

8 Claims, 3 Drawing Sheets

MOXIBUSTING IMPLEMENT

BACKGROUND OF THE INVENTION

1. Field of the Invention

The present invention relates to a moxibusting implement and more particularly, this invention is an improvement over Korean Utility Model application No. 98-3323 of which I am an inventor.

2. Description of the Prior Art

As shown in FIG. 4., the traditional moxibusting implement is manufactured by adhering an exfoliation paper(110) with a receiving hole(111) to a lower paper-board(120) with a receiving hole(121). A filter paper(130) is then adhered to on the lower paper-board and an upper paper-board(140) with a receiving hole (141) is adhered onto the filter paper in that order. Then a silver paper(150) with a receiving hole(151) is adhered to the upside of the upper paper-board and then a moxa(160) to the upside of the silver paper, respectively. The silver paper is adhered to the upside of the upper paper-board in order to prevent the upper paper board from igniting after a moxa is completely burned. However, this implement has many problems in that the silver paper is expensive and is neither burned up nor decays after use, which leads to environmental pollution. Also, since said moxibusting implement adheres the filter paper between the upper paper board and the lower paper board by applying adhesives to both board-papers, the filter paper could not perform its function practically due to the holes of the filter paper being clogged by the adhesive.

As shown in FIG. 5, said Korean utility model application No. 98-3323 has been filed prior to the filing of the present application in order to solve the above problems of said moxibusting implement. Said moxibusting implement(200) is manufactured by adhering non-woven fabric(220/230) to the upper and lower sides of a mud support(210) that has a receiving hole(211) and then adhering an exfoliation paper (240) to the lower side of the non-woven fabric(230) and then a moxa onto the non-woven fabric(220), respectively. However, said moxibusting implement has a drawback in that the non-woven fabric separates from the mud support due to the drying of the mud support with the passage of time.

SUMMARY OF THE INVENTION

One object of the present invention is to provide a moxibusting implement which can overcome the problems described above.

Another object of the present invention is to provide a moxibusting implement which has a remarkably superior effect in the moxa cautery treatment by the far-infrared radiation derived from the loess, yellow earth or dirt, or yellow mud, an improvement of filtration function, a sustained moxa cautery effect by residual heat after the complete combustion of moxa and no problem causing pollution due to complete combustion.

BRIEF DESCRIPTION OF THE DRAWINGS

The other objects and features of the present invention will be hereinafter explained in detail with reference to the accompanying drawings, wherein.

DESCRIPTION OF THE PREFERRED EMBODIMENTS

Figure 1:
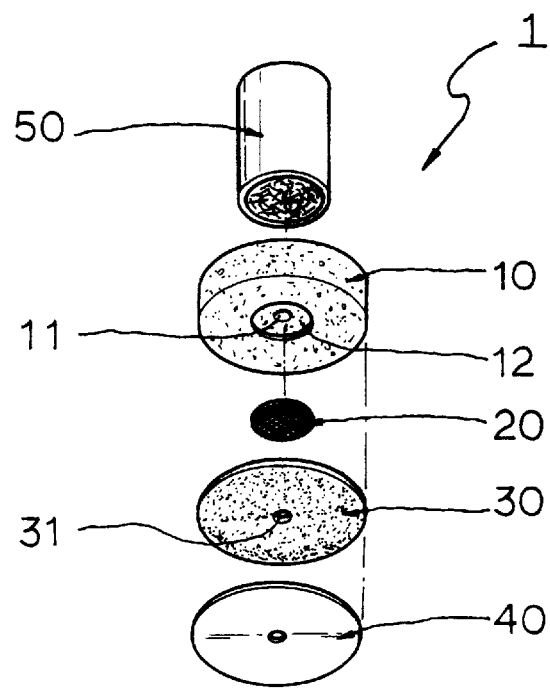
FIG. 1 is an exploded perspective view of a moxibusting implement according to the invention.
Figure 2:
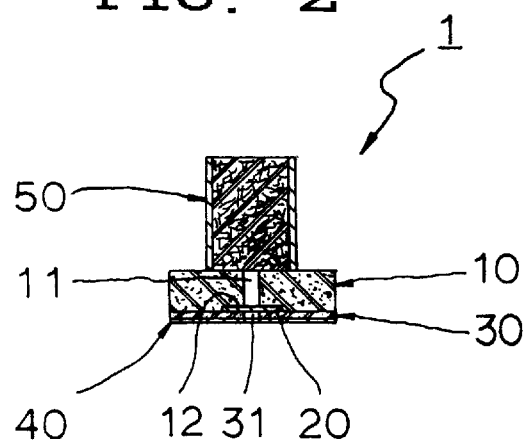
FIG. 2 is a cross-sectional view of a moxibusting implement according to the invention.
Figure 3:
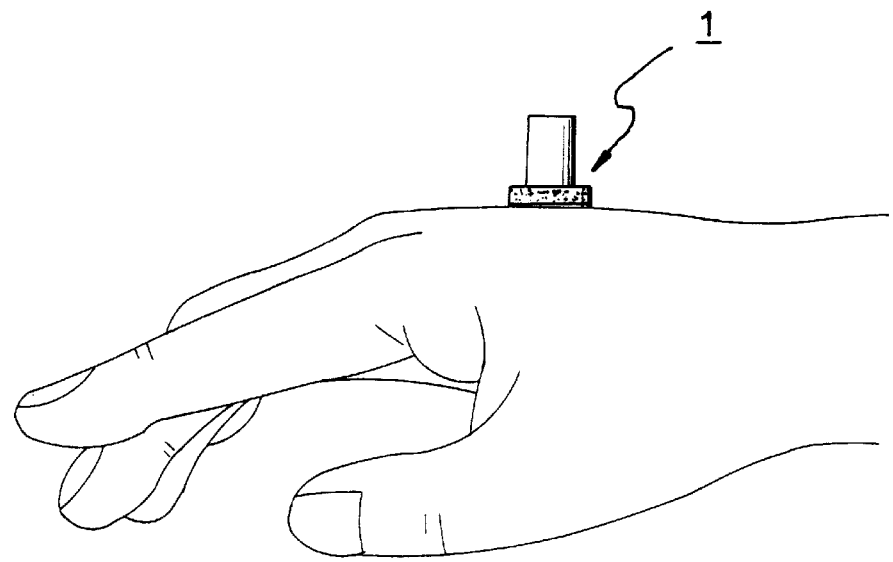
FIG. 3 is an illustrated view of the implement showing the state of operating.
Figure 4:
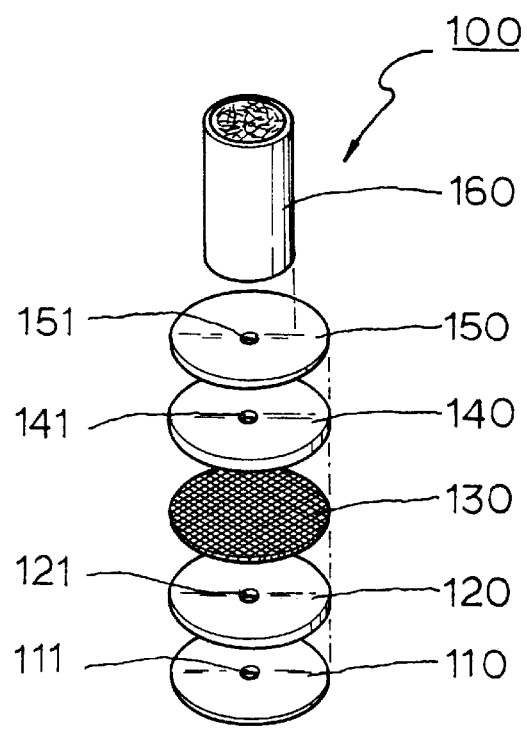
FIG. 4 is an exploded perspective view of a traditional moxibusting implement.
Figure 5:
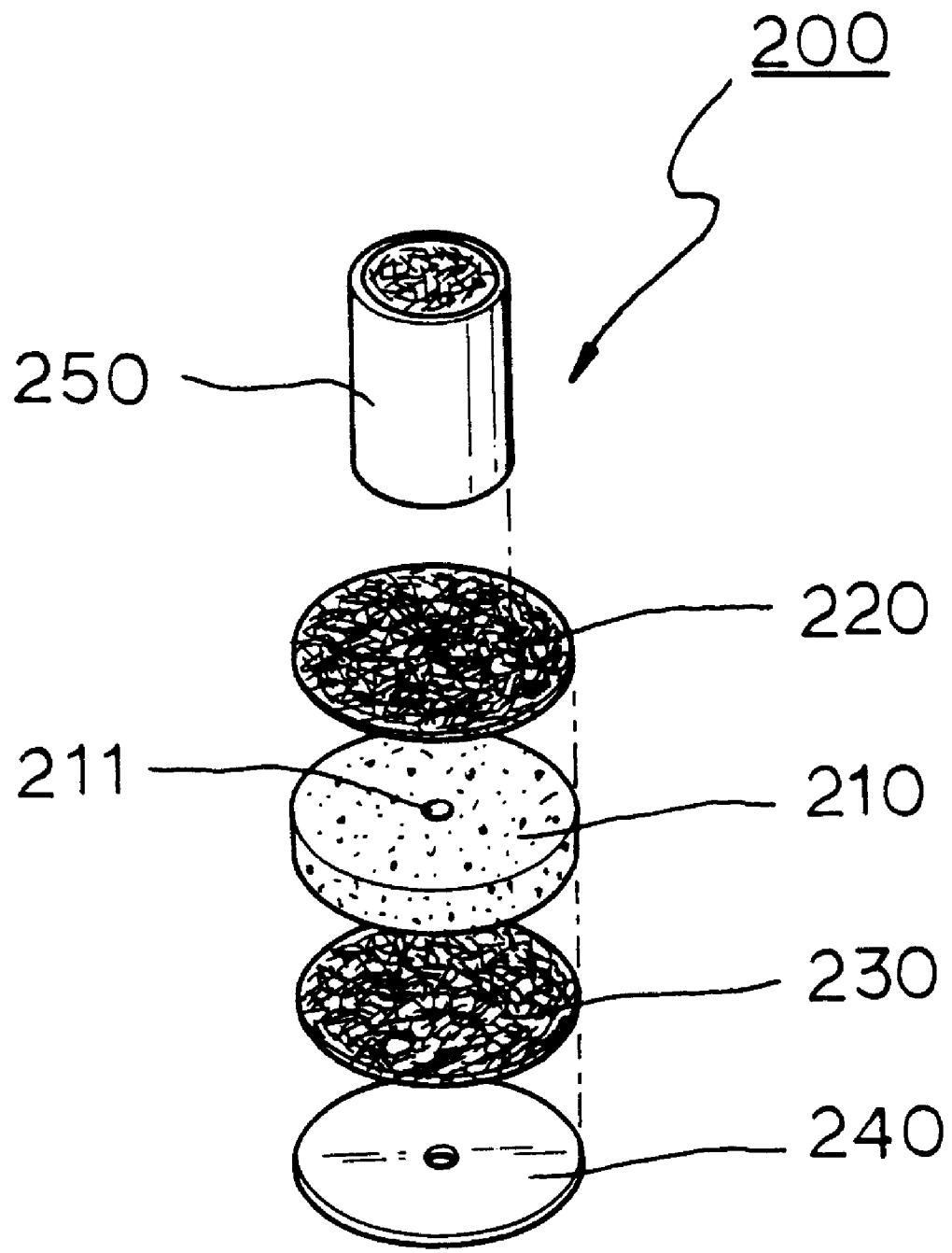
FIG. 5 is another exploded perspective view of a traditional moxibusting implement.

The moxibusting implement(1) according to the present invention is comprised of a support(10) made from loess, yellow earth or dirt, or yellow mud, having a receiving hole(11) and a groove or recess(12) with a predetermined outer shape and dimension in the center of the lower surface thereof, a filter paper(20) with said predetermined outer shape and dimension that closely fits within said groove(12), an adhesion sheet(30) having an upper adhesion layer adhered to the lower surfaces of said support(10) and said filter paper(20) and having a hole(31) therein, an exfoliation paper(40) secured to a lower surface of said adhesion sheet (30) and a moxa(50) positioned on the upper surface of said support(10).

After removing the exfoliation paper(40) adhered to the lower surface of the adhesive sheet(30), then adhering the implement at the skin surface and igniting the moxa(50), the heat and smoke occurring downwardly flows into the receiving hole(11). When the heat reaches the support(10), far-infrared radiation is produced from the support(10) and thereby a remarkably superior effect of the moxa cautery treatment is obtained. When heating it above a certain temperature, loess, yellow earth or dirt, or yellow mud produces far-infrared radiation. The filter paper inserted in the yellow mud is used to eliminate the wormwood resin and filter the heat passing through the yellow mud. The filter paper is fixed on the recess in the center of the lower surface of the yellow mud by the adhesive sheet. The effect of the moxa cautery treatment is sustained by residual heat even after complete combustion of moxa. Since the yellow mud support decomposes into earth, no pollution problem is caused when it is thrown away after use.

As mentioned above, this invention provides a moxibusting implement to enhance the effect of the moxa cautery treatment by employing a yellow mud support and improves the elimination of the wormwood resin by inserting and securing the filter paper into the recess in the yellow mud support. The moxibusting implement of the present invention also provides the sustained effect of the moxa cautery treatment and eliminates the pollution problem.

What is claimed is:

1. A moxibusting implement comprising:

a loess support having a receiving hole and a recess with a predetermined outer shape and dimension in a center of the lower surface thereof, a filter paper with said predetermined outer shape and dimension that closely fits within said recess, an adhesion sheet having an upper adhesion layer adhered to a lower surfaces of said loess support and said filter paper and having a hole therein, an exfoliation paper secured to a lower surface of said adhesion sheet, and a moxa positioned on an upper surface of said loess support.

2. A moxibusting implement according to claim 1, wherein said recess has a circular shape.

3. A moxibusting implement according to claim 1, wherein said recess is centrally positioned in the lower surface of the loess support.

4. A moxibusting implement according to claim 1, wherein said receiving hole is a through hole located along a central axis of said loess support.

5. A moxibusting implement according to claim 4, wherein said hole in said adhesion sheet is co-axially aligned with said receiving hole in said loess support.

6. A moxibusting implement according to claim 5, wherein said exfoliation paper has a hole which is co-axially aligned with said receiving hole in said loess support.

7. A moxibusting implement according to claim 1, wherein said moxa is aligned with said receiving hole of said loess support.

8. A moxibusting implement according to claim 7, wherein said receiving hole is a through hole located along a central axis of said loess support, and said moxa has a cylindrical configuration with a central axis in alignment with the receiving hole.

* * * * *